US011017897B2

(12) United States Patent
Soon-Shiong

(10) Patent No.: US 11,017,897 B2
(45) Date of Patent: May 25, 2021

(54) HEALTHCARE MANAGEMENT OBJECTS

(75) Inventor: Patrick Soon-Shiong, Los Angeles, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 383 days.

(21) Appl. No.: 14/006,935

(22) PCT Filed: Mar. 22, 2012

(86) PCT No.: PCT/US2012/030060
§ 371 (c)(1),
(2), (4) Date: Jan. 3, 2014

(87) PCT Pub. No.: WO2012/129372
PCT Pub. Date: Sep. 27, 2012

(65) Prior Publication Data
US 2014/0114675 A1 Apr. 24, 2014

Related U.S. Application Data

(60) Provisional application No. 61/466,400, filed on Mar. 22, 2011.

(51) Int. Cl.
*G16H 40/63* (2018.01)
*G16H 10/60* (2018.01)
(Continued)

(52) U.S. Cl.
CPC ............ *G16H 40/63* (2018.01); *G06Q 10/10* (2013.01); *G16H 10/60* (2018.01); *G16H 40/67* (2018.01)

(58) Field of Classification Search
CPC ...... G06F 19/321; G06F 19/322; G06F 21/32; G06Q 10/10; G06Q 50/22–24; H04L 63/105; G10L 17/14
See application file for complete search history.

(56) References Cited

U.S. PATENT DOCUMENTS 6,356,868 B1 * 3/2002 Yuschik .................. G10L 17/14
704/246
7,016,532 B2 3/2006 Boncyk et al.
(Continued)

FOREIGN PATENT DOCUMENTS

WO 2007127338 4/2010
WO 2010047695 A1 4/2010
(Continued)

OTHER PUBLICATIONS

HIPAA Resource GuideHealth Data Management 8.4: 107. SourceMedia, Inc. (Apr. 2000).*
(Continued)

*Primary Examiner* — Robert W Morgan
*Assistant Examiner* — Edward B Winston, III
(74) *Attorney, Agent, or Firm* — Stetina Brunda Garred and Brucker

(57) ABSTRACT

Healthcare object management systems and methods are presented. Health Object Identifiers (HOI) representative of healthcare object (e.g., medical records, data, etc.) can be derived from biometric data associated with a patient. HOIs can resolve to a network location where the healthcare object can be accessed. Biometric data, or other types of object data, can be exchanged among computing devices and the healthcare object. On exemplary use of HOIs includes self assembling personal data records as sensor data is obtained.

29 Claims, 2 Drawing Sheets

(51) Int. Cl.
*G06Q 10/10* (2012.01)
*G16H 40/67* (2018.01)

(56) References Cited

U.S. PATENT DOCUMENTS

| | | | |
|---|---|---|---|
| 7,181,617 B2* | 2/2007 | Wise | G16H 40/67 |
| | | | 713/164 |
| 7,421,399 B2* | 9/2008 | Kimmel | G06Q 10/10 |
| | | | 705/3 |
| 7,477,780 B2 | 1/2009 | Boncyk et al. | |
| 7,564,469 B2 | 7/2009 | Cohen | |
| 7,565,008 B2 | 7/2009 | Boncyk et al. | |
| 7,593,549 B2 | 9/2009 | Reiner | |
| 7,668,734 B2 | 2/2010 | Pugh | |
| 7,680,324 B2 | 3/2010 | Boncyk et al. | |
| 7,685,417 B2 | 3/2010 | Wise et al. | |
| 7,760,905 B2 | 7/2010 | Rhoads et al. | |
| 7,814,035 B2 | 10/2010 | Mundie et al. | |
| 7,941,324 B1 | 5/2011 | Sholtis | |
| 7,970,620 B2 | 6/2011 | Brown | |
| 8,086,470 B2 | 12/2011 | Siegel | |
| 8,751,816 B2* | 6/2014 | Simske | G06F 21/32 |
| | | | 713/186 |
| 9,405,814 B1* | 8/2016 | Kapoor | G06F 16/256 |
| 2003/0217005 A1* | 11/2003 | Drummond | G06Q 30/06 |
| | | | 705/43 |
| 2004/0111530 A1 | 6/2004 | Sidman | |
| 2004/0148503 A1 | 7/2004 | Sidman | |
| 2006/0004604 A1* | 1/2006 | White | G16H 10/65 |
| | | | 705/2 |
| 2006/0064326 A1* | 3/2006 | Tucker | G06Q 40/08 |
| | | | 705/3 |
| 2007/0109266 A1 | 5/2007 | Davis et al. | |
| 2007/0192872 A1 | 8/2007 | Rhoads et al. | |
| 2007/0198432 A1 | 8/2007 | Pitroda et al. | |
| 2008/0086337 A1 | 4/2008 | Soon-Shiong | |
| 2008/0126417 A1* | 5/2008 | Mazurik | G06F 16/80 |
| 2008/0181465 A1 | 7/2008 | Sauerwein | |
| 2008/0183497 A1 | 7/2008 | Soon-Shiong | |
| 2009/0070148 A1* | 3/2009 | Skocic | G06F 16/9537 |
| | | | 705/3 |
| 2009/0076840 A1* | 3/2009 | Boyden | G16H 40/67 |
| | | | 705/2 |
| 2009/0172781 A1* | 7/2009 | Masuoka | H04L 63/105 |
| | | | 726/3 |
| 2010/0169642 A1 | 7/2010 | Wise et al. | |
| 2010/0211552 A1 | 8/2010 | Sidman | |
| 2010/0281364 A1 | 11/2010 | Sidman | |
| 2011/0029674 A1 | 2/2011 | Sidman | |
| 2011/0119075 A1* | 5/2011 | Dhoble | G16H 10/60 |
| | | | 705/2 |
| 2011/0288874 A1 | 11/2011 | Hinkamp | |
| 2011/0289572 A1 | 11/2011 | Skeel et al. | |
| 2012/0004525 A1 | 1/2012 | Brown | |

FOREIGN PATENT DOCUMENTS

| | | | | |
|---|---|---|---|---|
| WO | WO-2010047695 A1 * | 4/2010 | | G06F 21/32 |
| WO | 2010135578 A2 | 11/2010 | | |

OTHER PUBLICATIONS

ISA/KR, International Search Report and Written Opinion for International Appln. No. PCT/US2012/030060; dated Sep. 26, 2012; 10 pages.
"Examination Report under Section 18(3)" dated Aug. 11, 2017. GB1316565.9, 8 Pages.

* cited by examiner

HEALTHCARE MANAGEMENT OBJECTS

This application claims the benefit of priority to U.S. provisional application having Ser. No. 61/466,400 filed on Mar. 22, 2011. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is healthcare data management technologies.

BACKGROUND

Gaining access to medical records can become quite problematic due to many regulatory issues. Although it is known to use biometric data to authenticate a patient such as that described in U.S. Pat. No. 7,593,549 to Reiner and U.S. patent application publication 2011/0288874 to Hinkamp (publ. November 2011), unfortunately, typical patients visit many different healthcare providers, resulting in the patient's medical records being distributed across many disjoint or disconnected databases. In such an environment, patients lack access to their medical records or even lack authorization to their own records. Many other organizations and entities have attempted to address such access issues by storing medical records in a medical record clearing house or storing records local to a healthcare provider while allowing others to see only metadata associated with remotely stored medical records. Even still, a patient has a great deal of difficulty gaining access, or just providing access, to their medical records. A better approach would allow patients to access or even update their own records on a record-by-record or even field-by-field basis where each record can be individually addressed via a Health Object Identifier (HOI), especially in environments where biometric data is obtained from a patient in real-time.

Generic objects can be addressed by an object identifier via a Digital Object Identifier (DOI®) as proposed by The International DOI Foundation (see URL www.doi.org). Others have proposed many uses for DOIs. For example, U.S. patent application publication 2004/0111530 to Sidman (publ. June 2004) references providing access to medical records via a DOI.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It has yet to be appreciated one can derive a HOI based on biometric data associated with a patient. As discussed herein with respect to the inventive subject matter, biometric sensor systems can obtain the biometric data from the patient and identify a corresponding HOI to be used in conjunction with the biometric data. For example, the HOI can be used as a pointer to where the biometric data should be stored or as a location for retrieval. Thus, the applicants have appreciated that a medical record having a corresponding HOI can be auto-assembled, even in real-time, as biometric data is obtained.

Thus, there is still a need for health object identifier management systems.

SUMMARY OF THE INVENTION

The inventive subject matter provides apparatus, systems and methods in which one can acquire biometric data and convert the biometric data into a healthcare management object. One aspect of the inventive subject matter includes a health object identifier (HOI) management system where biometric data is collected via a biometric interface. Exemplary biometric interfaces can include a suitably configured sensor, mobile phone, portable computer, garment, server, or other device capable of acquiring data. For example, a server can comprise one or more web-based application programming interfaces (APIs) through which a cell phone can send captured bio-sensor data. A conversion module within the management system derives a HOI from at least portions of the captured biometric data associated with a patient. More preferred HOIs comprises a patient identifier portion, possibly a prefix, and an object portion, possibly a suffix. The combined portions preferably represent a unique identifier associated with a health care object to be associated with or bound to the biometric data. HOIs can define a network location of a health care object including, for example, a medical record or even a specified field in a record.

Another aspect of the inventive subject matter includes methods of assembling a personal data record. Contemplated methods include providing access to a biometric sensor that is capable of acquiring biometric data associated with a patient. The biometric sensor can be coupled with a sensor hub, which obtains access to the biometric data and derives a HOI based on at least a portion of the data. The sensor hub can also transmit the biometric data over a network to a location specified by the HOI. Exemplary sensor hubs can include a mobile device, a cell phone, a vehicle, a suitably adapted garment, or other computing device. In some embodiments, the sensor hub operates as a temporary data store until network connectivity allows for exchanging biometric data with a location specified by the HOI.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
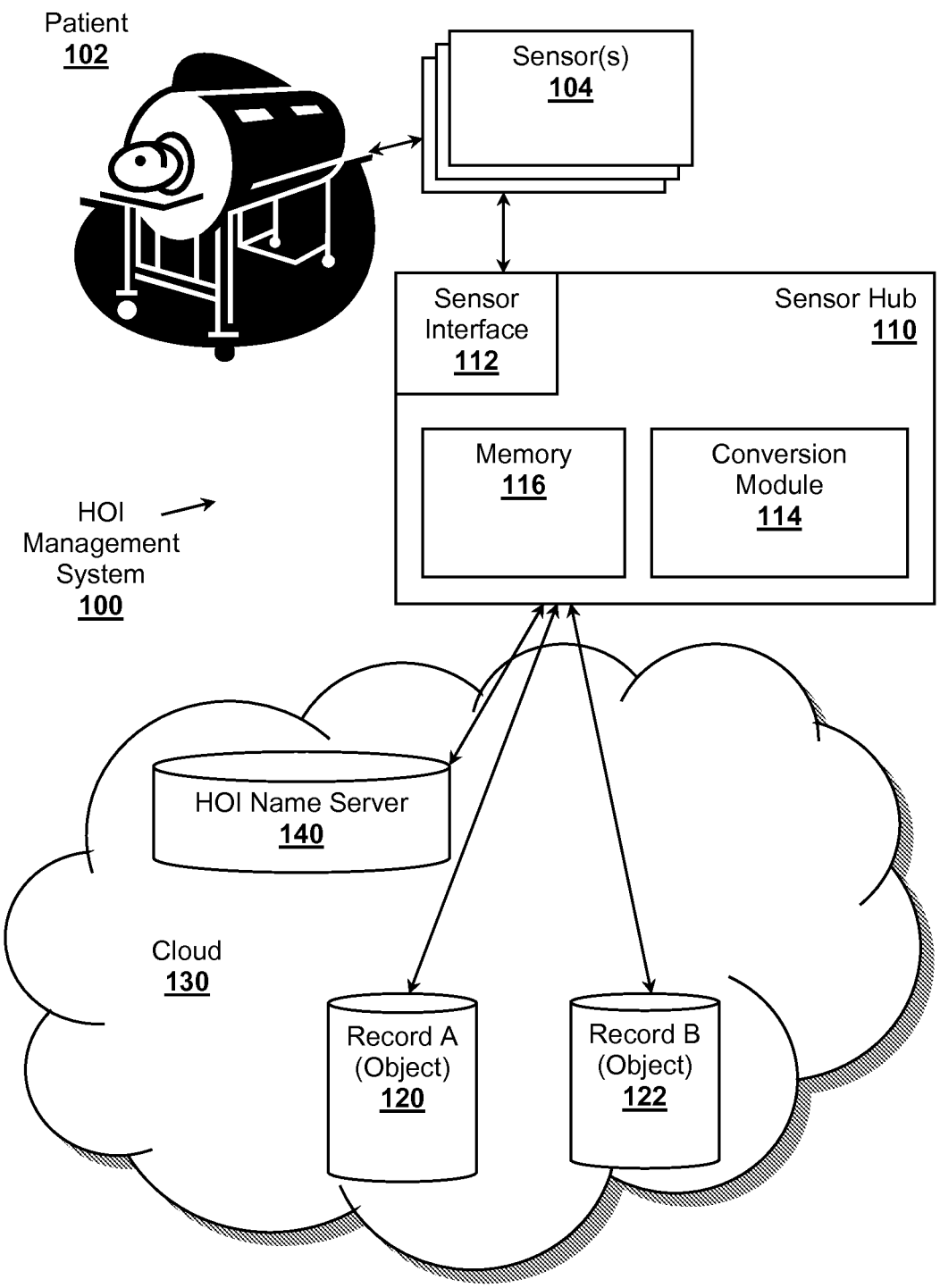
FIG. 1 is a schematic of an embodiment of a health object management system.

It should be noted that while the following description is drawn to a computer/server based health care object management system, various alternative configurations are also deemed suitable and may employ various computing devices including servers, interfaces, platforms, peers, systems, databases, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.).

The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including using sensor signals to configured a healthcare data network to route data from one or more of the sensors into a remote database housing data records. Contemplated systems also provide an infrastructure for self-assembling medical records over a network based on the signals generated by the sensors.

Although the following discussion is directed to patient-centric healthcare objects, one should appreciate that the disclosed techniques can also be applied other types of data objects. Exemplary types of objects can include experimental or science data objects, media objects, course work objects, game related objects, augmented reality objects, or other types of objects.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document the terms "coupled to" and "coupled with" are also used to mean "communicatively coupled with" over a network, possibly via one or more intermediary networking nodes.

The following discussion provides many example embodiments of the inventive subject matter. Although each embodiment represents a single combination of inventive elements, the inventive subject matter is considered to include all possible combinations of the disclosed inventive elements. Thus if one embodiment comprises elements A, B, and C, and a second embodiment comprises elements B and D, then the inventive subject matter is also considered to include other remaining combinations of A, B, C, or D, even if not explicitly disclosed.

In FIG. 1, a HOI management system 100 is configured to provide access to a medical record based on biometric data acquired from a patient. One or more sensors 104 capture biometric or other sensor data associated with the patient 102. Contemplated patients could include, for example, an athlete or other human, a pet or other animal, and so forth. A sensor hub 110 acquires the sensor data via a sensor interface 112 and uses a conversion module 114 to derive or otherwise identify a HOI to be associated with the sensor data. In some embodiments, the sensor data can be stored in a secured memory 116, possibly secured according to the FIPS 140 standard, or container within the sensor hub 110. When connectivity permits, the sensor data can exchanged with an object 120 representing a medical record located on a network 130 at an address referenced by the HOI. In some embodiments, a virtual machine can be instantiated based on the HOI or its information to manipulate or store the data. In the example shown, medical records comprise objects 120 and 122 located on a cloud network, which could include the Internet, server farm, personal area network, local area network, wireless network, or other type of network. Although sensor data is exchanged with medical record objects, one should also appreciate that the data can also be obtained from the objects via use of the HOI.

Sensors 104 used to capture biometric data, or the type of data for that matter, cover a broad spectrum of data capture devices. More preferred sensors capture health related data associated with a patient (e.g., a human, an animal, etc.). Exemplary medical sensors can include perfusion sensors, brain wave sensors, heart rate sensors, thermometers, EKGs, movement sensor, or other types of health monitoring sensors. Although more preferred sensors capture medical related data, it is also contemplated that non-medical sensors can be used to capture data related to a patient. Exemplary non-medical sensors include accelerometers, magnetometers, GPS, cameras for capturing visible or non-visible data, microphones, spectrometers, seismometers, chemical sensors (e.g., $CO_2$, pH, etc.), hall probes, flow or fluid sensors, radiation sensors, navigation sensors, position or orientation sensors, pressure sensors, optical sensors, force or density sensors, proximity sensors, or other types of sensors.

Biometric data acquired by the sensors can also cover a broad spectrum of data types ranging from modalities that fall within the scope of human experience to modalities outside the human experience (e.g., radiation, non-visible parts of the electromagnetic spectrum, etc.). The biometric data is considered to include a digital representation of at least a portion of the patient 102. Examples comprise digital representations of a face, a fingerprint, an iris, a vital sign, a brain signal, a voice, genomic or proteomic information, or other aspects of the patient 102. In some embodiments such biometric data carry patient identity information. For example, sensor hub 110 can evaluate an image of the patient's face or signature to determine the identity of the patient 102. It is also contemplated that data beyond a face, fingerprint, or signature can also be used to determine identity of the patient 102. Brain waves, for example, could be used to identify the patient. Further, a sensor signature related to a person's walking or talking pattern could be used to identify the patient. Even genomic information could be used to identify the patient portion of an HOI.

The sensor hub 110 operating as a biometric interface can acquire the biometric data from one or more sensors 104. The sensor hub 110 can include a device local to the patient 102 or even a computing device located at a remote location, possibly geographically separated from the patient 102. In some embodiments, the sensor hub 110 comprises a mobile device (e.g., a mobile phone, vehicle, etc.) local to the patient 102, possibly operating as a member of a sensor web or a personal area network. For example, the patient's cell phone can comprise one or more sensors that monitor the health of the patient 102. In other embodiments, the sensor hub 110 can comprise a remote web service that provides access to web-based APIs through which sensors 104 submit their data.

Preferably, the HOI management system 100 also includes a conversion module 114 coupled with the biometric interface and configured to identify a relevant HOT associated with the biometric data. The conversion module 114 can be configured to evaluate at least some of the biometric data in an attempt to derive or otherwise identify a HOI to be used in conjunction with the biometric data. Preferred HOIs have a portion that is patient specific and a second, different portion that is object specific. Such HOIs allow for having many objects associated with a single patient. The patient identifier portion of the HOI can be derived from recognizing aspects of the patient 102 from the biometric data. For example, an image of the patient's face can be recognized. Once recognized the patient identifier portion can be looked up in a patient database. Many alternative approaches can also be leveraged to derive the patient identifier portion of the HOI. For example, a hash function can be applied to the biometric data (e.g., signature, fingerprint, face, brain signals, etc.) where the resulting hash value can be the patient identifier portion. Suitable techniques for object recognition that can be adapted for use to identify a patient from image data or other type of data are described in U.S. Pat. Nos. 7,016,532; 7,477,780; 7,680, 324; 7,565,008; and 7,564,469. All mappings or derivations from biometric data to a patient identifier portion are contemplated.

The conversion module 114 can also derive or identify an object identifier portion of the HOI. The module 114 can derive the object identifier portion based on the biometric data. For example, the biometric data can comprises metadata about the source of the data where the metadata provides instructions on conversion of the metadata into the object identifier portion. In some embodiments, the type of sensor data determines the object identifier. Alternatively, the sensor data could include encoded object identifier information, perhaps a sensor ID, which becomes the object identifier. All possible mappings of sensor data to object identifiers are contemplated.

As stated above, more preferred HOIs include a patient identifier portion and an object identifier portion where the combined identifier portions can be used to reference a network location corresponding to an object (e.g., record 120). In some embodiments, HOIs conform to Digital Object Identifiers (DOIs®) where the prefix of a DOI comprises the patient identifier and the suffix comprises the object identifier. In yet other embodiments, a HOI can comprise a URL or other form of network address. In such embodiments, a domain name of the URL can be representative of the patient identifier portion and the link portion of the URL can comprise the object identifier portion of the HOI. Portions of the HOI can also be derived from other types of data possibly including data related to a bar code (e.g., 1D, 2D, QR Codes, proprietary codes, etc.), a pattern, a RFID tag, an alpha-numeric string, a logo, a symbol, or other types of data.

A HOI can be resolved to a network location by a HOI resolution engine 140 that is coupled with the conversion module 114. When a computing device wishes to access an object identified by a HOI, the computing device submits the HOI to a resolution engine 140, which in turn resolves the HOI to an actual health object location on a network 130, for example. In most embodiments, the HOI resolves to a network address (e.g., URL, IP address, storage device, etc.). In the example shown, the HOI resolution engine 140 is illustrated as a HOI name server, which could include, for example, a DOI resolver (e.g., the domain dx.doi.org) or one or more DNS servers. As part of the HOI resolution process, the HOI resolution engine 140 can redirect an object request to an appropriate network location.

In the example shown, the objects 120 and 122 reside in a network cloud 130 where the network locations of each of the objects 120 and 122 can be represented by a URL, an internet location, a protocol, a link, a unique identifier (e.g., GUID, UUID, etc.) or other type of network address. However, the network 130 does not necessarily have to be remote relative to the patient 102, but could also be local to the patient 102. In some embodiments, the network 130 can comprises a personal area network where the network location resolves to a personal area network location local to the patient 102, a memory location, or even a storage location. When the system 100 establishes connectivity with external networks, the sensor hub 110 or other device can cause the locally stored object data to migrate to remote object locations. In fact, the inventive subject matter is considered to include seamlessly managing HOIs or objects even when network connectivity is intermittent. For example, when connectivity is down, the sensor hub 110 can derive a HOI and determine it should, at least temporarily, resolve to memory 116 (e.g., a secured memory location, secured container, secured virtual machine, etc.). When connectivity is restored, the HOI would resolve normally to an external network location.

Once the network location of a HOI-referenced object is known, the sensor hub 110 or other device(s) can access the object (e.g., record 120) directly. In some embodiments, the object can be accessed as a data source (e.g., a sensor, a storage device, etc.) via the HOI through which object data can be obtained, while in other scenarios the object can be accessed as a data sink (e.g., memory, storage device, etc.) via the HOI where object data can be stored. Thus an HOI is can point to a data consumer (e.g., storage location, analysis engine, etc.) or point to a data source (e.g., sensor, sensor hub, etc.).

An object access request can come from many different sources including, for example, devices, patients, healthcare providers, or other entities. For example, a doctor might request access to a patient's sensor data. The doctor could use a mobile device, such as an iPad™ running a suitable app, for example, to capture an image of the patient where the mobile device derives a patient identifier from the image. The patient could provide an object identifier, possibly in the form of a sensor identifier, to the doctor's device perhaps in a secure format to maintain privacy. The doctor's device then can access data streaming directly from the patient's sensors. It should be appreciated that a HOI can be derived from the access request, which can include biometric data, regardless if the request is to write data to or read data from the object.

Figure 2:
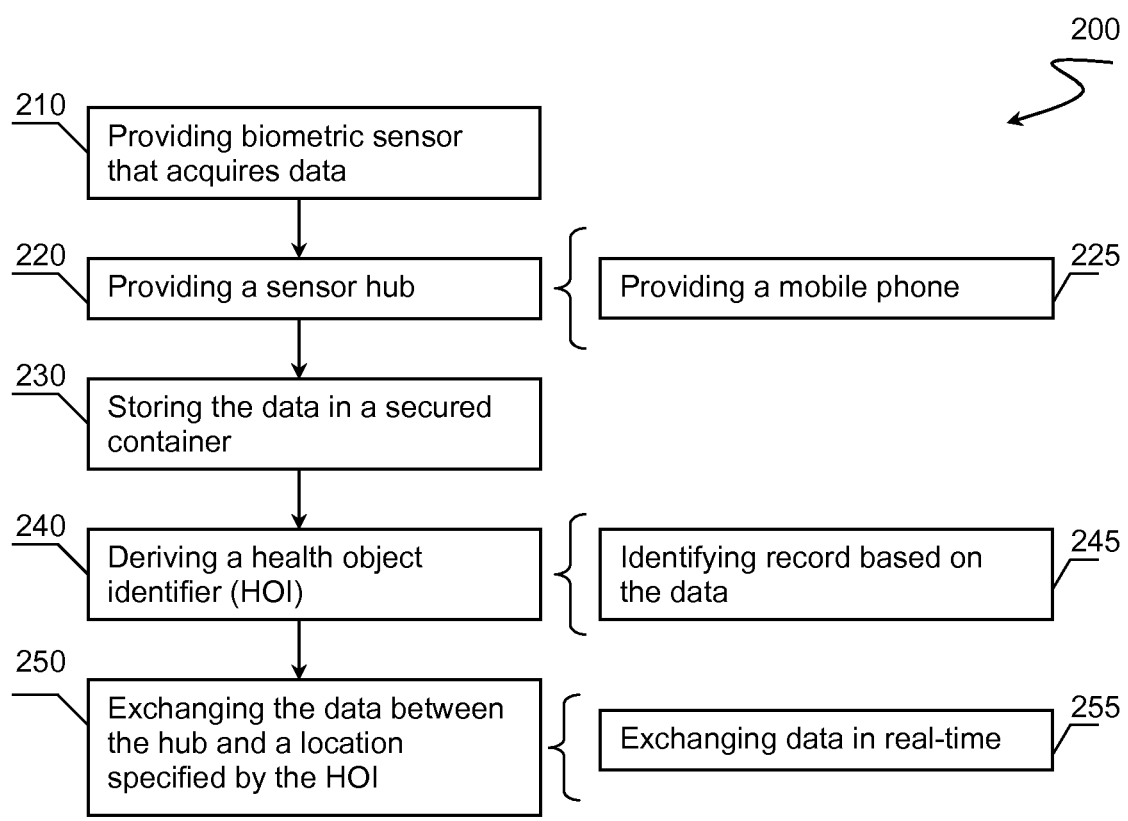
FIG. 2 is one embodiment of a method for assembling a data record from sensor data.

FIG. 2 presents possible method 200 for assembling a personal data record, a medical record for example, based on the above-mentioned inventive concepts. Step 210 includes providing a biometric sensor configured to acquire biometric data associated with a patient. The sensor can be directly or indirectly attached to the patient as desired. In some embodiments, the sensor can be incorporated in a mobile device including, for example, a cell phone, vehicle, or portable computer. Exemplary sensors include perfusion sensors, brain wave sensors, heart rate sensors, thermometers, EKGs, movement sensor, accelerometers, magnetometers, GPS, cameras for capturing visible or non-visible data, microphones, spectrometers, seismometer, chemical sensors (e.g., $CO_2$, pH, etc.), hall probes, flow or fluid sensors, radiation sensors, navigation sensors, position or orientation sensors, pressure sensors, optical sensors, force or density sensors, proximity sensors, or other types of sensors.

One should note that the term "providing" is used euphemistically to represent generically making available. Providing an item can include manufacturing, selling, exposing an API, or other form of making a component or its capabilities available to a user.

Step 220 includes providing a sensor hub coupled with one or more sensors. The sensor hub preferably comprises a computing device capable of acquiring sensor data from the one or more sensors. The sensor hub can operate as a biometric interface through which sensor data can be exchanged with other computing devices as desired. The sensor hub can have a sensor integrated into the hub or can access sensors through wired connections or wireless connections (e.g., RF, Bluetooth, Wi-Fi, WiGIG, etc.). Exemplary sensor hubs can comprise mobile devices (e.g., mobile phones, vehicles, etc.) or other types of computing devices.

In some embodiments, the sensor hubs can include networking infrastructure possibly include switches, routers, gateways, or other infrastructure. For example, switches deployed within the National Lamba Rail (see URL www.nlr.net) could operate as one or more sensor hubs capable of acquiring sensor data. Each switch can determine the HOI for a patient's data as the biometric data flows through the network.

To further enhance security, each patient's data can be secured for processing by instantiating a virtual machine specific to the individual where the characteristics of the virtual machine are determined from the derived HOI. For example, during intermittent connectivity a cell phone can instantiate a secured virtual machine that security stores patient data. The virtual machine remains in existence until it can download/upload its data to the proper HOI. Another example includes instantiating a virtual machine on a network switch that controls rendering, display, or otherwise forwarding the data to a proper record addressed by the HOI. Example techniques for instantiating virtual machines that can be adapted for use with the inventive subject matter include U.S. Pat. Nos. 7,181,617; 7,685,417; and U.S. patent application publication 2010/0169642. In yet more preferred embodiments involving virtual machines, a virtual machine is instantiated where the HOI resolves to a location in the memory of the virtual machine. Thus, as sensor data is acquired and a corresponding HOI is derived, the system can instantiate a patient-specific virtual machine that can be under control of the sensor hub where the sensor data is forwarded to the virtual machine as a function of the HOI. One should appreciate that a virtual machine can operate as a sensor hub or as a destination of data as desired.

In some contemplated embodiments, step 230 includes storing sensor data within a secured container such as a memory of the sensor hub. For example, a doctor might collect biometric data from a patient via a portable computer (e.g., an iPad™, XOOM™, etc.). The portable computer can configure a section of memory as a secured container where data is stored in an encrypted format to ensure the patient's data remains private. A secured memory container can be secured according to one or more standards, including FIPS 140-2 for example.

Step 240 comprises deriving a HOI corresponding to the patient based on at least a portion of the biometric data. As discussed above, one or more portions of the HOI, including a patient identifier portion can be identified from the biometric data. To continue the example of a doctor capturing patient biometric data, the doctor can capture an image of the patient where the image data can be evaluated to determine the patient's identity. In some embodiments, a patient identifier portion of the HOI could include a vector of image features where each element of the vector represents an aspect of the image (e.g., color, contrast, histogram, imaged feature location, etc.). Existing algorithms (e.g., SIFT, SURF, ViPR, vSLAM, etc.) can be applied to create such a signature vector. This signature vector can them map to one the patient identifier. Although an image of the patient is used as an example, one should appreciate the signature vector can comprise multiple modalities of data types possibly including iris data, fingerprint data, voice data, genomic data, behavior pattern data, or other types of data.

In addition to identifying the patient, step 245 can include deriving an object identifier portion of the HOI, which represents a specific record object or record field object associated with the patient. HOIs are preferably capable of resolving to an object location on a network where the object comprises a personal record of the patient. HOIs can comprises a domain name, a DOI, a URL, a URI, a unique identifier, a link, or even a URI scheme to be used to access the object (e.g., http://, https://, ftp://, ssh://, telnet://, sip://, nfs://, mailto://, file://, sms://, etc.).

Step 250 includes exchanging sensor data between the sensor hub and an object representing the patient's personal data record. The sensor data, or other object data, can be exchanged over a network depending on the location of the personal data record object and the sensor hub. In some embodiments, the sensor hub houses the record object within a local memory, possibly on a temporary basis, while in other scenarios the record object can be located remotely over a network. The data exchange can occur over a personal area network, local area network, wide area network, the Internet, wired networks, wireless networks, cell networks, or other types of networks.

One should appreciate that the sensor hub can include a conversion module configure to convert the sensor data from a first format to second format associated with the destination referenced by the HOI. In some scenarios the conversion module can analyze or convert raw sensor data a specific format determined from the object identifier portion of the HOI. A simple example could include obtaining sensor data from a patient's garments, temperature or respiration rate for example, The sensor hub can receive the raw data and derive one or more corresponding HOIs based on the biometric data and the type of sensor data. The sensor hub can create a comma separated value (CSV) file of the data and forward the data to a remote virtual machine configure to accept the CSV file. Although the preceding is a simply example, one should a appreciate that the conversion module can further select the desired rules or algorithms for conversion or analysis based the patient identifier portion of the HOI, the object identifier portion HOI, or a combination of both.

As suggested by step 255, the data exchange between the sensor hub and the object can occur in real-time relative to the time when the sensor data is acquired. For example, a patient's cell phone can monitor one or more health metrics and exchange the collected metrics with the patient's medical record object possibly located temporarily on a doctor's portable computer. Thus the patient's medical record can be auto-assembled in real-time.

The following examples will aid the reader in gaining further understanding of the disclosed techniques. Consider a runner wearing an instrumented running shoe having a sole with active sensors. The sole of the shoe can be configured to transmit sensor data from the shoe to the runner's cell phone, for example. The cell phone uses information about the runner, a fingerprint for example, and the shoe sensor data to derive a HOI indicating a location of the runner's log on a remote server. As the shoe collects the sensor data, the data can temporarily be stored on the cell phone or forwarded on to the runner's log. Furthermore, the sensor itself could be considered an object having its own HOI. Thus the sensor data could be obtained via a push from the cell phone or a pull from the runner's log.

Another example could include monitoring brain functions of a patient. One or more sensors can monitor ten, 100, 1000, or more data channels providing data representative of the patient's current brain activity. The sensors, or sensor array, can be assigned a HOI, which can be accessed by a doctor or lab equipment via use of the HOI. Alternatively, the brain activity could be evaluated to determine the patient's identity, possibly through an identity signature derived from brain signals. The data can be collected and evaluated to derive a HOI representing a database where the data is to be stored. Data can be aggregated and collected via a wireless connection (e.g., WiGIG, Wi-Fi, etc.) and sent to the database as indicated by the HOI.

Numerous advantages arise from the disclosed techniques. Patients are able to maintain control over their personal data records through controlled access of portions of the HOIs. The patient identifier portion of a HOI can be derived from the patient's image, fingerprint, signature, brain waves, voice, or other identifying features alone or in combination. However, the object identifier portion of the HOI can be kept secret. Furthermore, the patient could interface with the HOI management system to define HOIs for their data records or other digital objects associated with the patient. Another advantage includes allowing doctors or other healthcare providers to access healthcare objects based on the HOIs in a secure fashion. For example, a doctor could prepare for a patient meeting by accessing the records via a HOI and storing the patient's records locally in a mobile device's secured memory, virtual machine, assuming proper authorization by the patient. As the doctor interacts with the patient, acquired data can be stored locally by the same HOI, which temporarily maps to the mobile device's memory. When appropriate, the HOI can again map to the actual record's location on the network. Such an approach ensures data can be accessed quickly when needed without risking loss of connectivity when the data is needed most.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer based health object identifier (HOI) management system, comprising:
   a biometric interface configured to acquire biometric data associated with a patient, the biometric data comprising medical sensor data, the biometric interface comprising a computing device having at least one sensor;
   a conversion module coupled with the biometric interface and configured to identify a patient-specific health object identifier (HOI) comprising a patient identifier portion as a prefix portion and an object identifier portion as a suffix portion, where the patient identifier portion is specific to the patient and the object identifier portion is specific to a medical record of the patient to contain the medical sensor data, the patient identifier portion being at least in part derived from the biometric data, the object identifier portion being at least in part derived from the medical sensor data, wherein the patient-specific HOI forms a single address defined by the prefix and suffix portions and that is resolvable to a unique network location via a domain name server; and
   a HOI resolution engine coupled with the conversion module and configured to, upon receipt of the patient-specific HOI from the computing device, resolve the patient-specific HOI to an object location over a network at the unique network location based on the single address defined by the prefix and suffix portions;
   wherein the computing device writes the medical sensor data to the object location in real-time when the medical sensor data is acquired to auto-assemble the medical record of the patient.

2. The system of claim 1, wherein the biometric data comprises a digital representation of a portion of the patient.

3. The system of claim 2, wherein the portion of the patient includes at least one of the following: a face, a fingerprint, an iris, a vital sign, a voice, and a brain signal.

4. The system of claim 1, wherein the computing device comprises a mobile device.

5. The system of claim 4, wherein the mobile device comprises a mobile phone.

6. The system of claim 4, wherein the mobile device comprises a vehicle.

7. The system of claim 1, wherein the sensor comprises at least one of the following types of sensors: a light sensor, a bio-sensor, an audio sensor, a pressure sensor, a perfusion sensor, and a heart sensor.

8. The system of claim 1, wherein the object location resolves to at least one of a personal area network location, an internet location, a memory location, and a storage location.

9. The system of claim 1, wherein the HOI resolution engine resides within a mobile device.

10. The system of claim 1, wherein the HOI resolution engine comprises a distal server.

11. The system of claim 1, wherein the HOI comprises at least one of the following: a domain name, a digital object identifier, a URL, a unique identifier, a protocol, and a link.

12. The system of claim 1, wherein the object identifier portion is further at least in part derived from at least one of the following: a bar-code, an RFID tag, an alpha-numeric string, a logo, metadata, and a symbol.

13. The system of claim 1, wherein said conversion module is further configured to instantiate a virtual machine to securely store medical sensor data, where the characteristics of the virtual machine are determined, at least in part, by the derived HOI.

14. The system of claim 1, said conversion module further configured to instantiate a virtual machine to process the medical sensor data, wherein the characteristics of the virtual machine are determined, at least in part, by the derived HOI.

15. The system of claim 1 wherein said biometric interface further comprises a memory for storing the medical sensor data in an encrypted format.

16. The system of claim 1 wherein said object identifier portion is further at least in part derived from sensor identification information.

17. The system of claim 1 wherein the medical sensor data is selected from the group consisting of perfusion sensor data, brain wave sensor data, heart rate sensor data, thermometer data, EKG data, and movement sensor data.

18. The system of claim 1 wherein the single address is a URL, and the prefix is a domain name of the URL.

19. The system of claim 1 wherein the patient identifier portion includes a vector of image features.

20. The system of claim 1 wherein the conversion module derives the object identifier portion from metadata of the biometric data that describes the source of the biometric data.

21. The system of claim 1 wherein the computing device submits the medical sensor data to the conversion module using an API.

22. A method of assembling a personal data record over a computer based network, comprising:
   providing at least one sensor configured to acquire biometric data associated with a patient, the biometric data comprising medical sensor data;
   providing a sensor hub coupled with at least one sensor;
   deriving a patient-specific health object identifier (HOI) corresponding to the patient based on the biometric data wherein said patient-specific HOT comprises a patient identifier portion as a prefix portion that is specific to the patient and an object identifier portion as a suffix portion that is specific to a medical record of the patient to contain the medical sensor data, the patient identifier portion being at least in part derived from the biometric data, the object identifier portion being at least in part derived from the medical sensor data, wherein the patient-specific HOI forms a single address defined by the prefix and suffix portions and that is resolvable to a unique network location via a domain name server;
   resolving the patient-specific HOI to an object location over a network at the unique network location based on the single address defined by the prefix and suffix portions; and
   writing the medical sensor data to the object location specified by the patient-specific HOI over the network in real-time when the medical sensor data is acquired to auto-assemble the medical record of the patient.

23. The method of claim 22, wherein the HOI comprises at least one of the following: a domain name, a digital object identifier, a URL, a unique identifier, a protocol, and a link.

24. The method of claim 22, where the step of providing a sensor hub comprises providing a mobile phone.

25. The method of claim 22, further comprising storing the medical sensor data in a secured container within a memory of the sensor hub.

26. The method of claim 22, wherein the step of writing the medical sensor data includes exchanging the medical sensor data over at least one of the following networks: a personal area network, a local area network, a wide area network, the Internet, and a wireless network.

27. The method of claim 22 further comprising the step of securely storing the medical sensor data for processing by instantiating a virtual machine where the characteristics of the virtual machine are determined, at least in part, by the derived HOI.

28. The method of claim 22 further comprising the step of storing the medical sensor data in an encrypted format.

29. A non-transitory computer readable medium on which are stored instructions executable by a processor to perform operations for assembling a personal data record, the operations comprising:
   acquiring biometric data associated with a patient, the biometric data comprising medical sensor data;
   identifying a patient-specific health object identifier (HOT) comprising a patient identifier portion as a prefix portion and an object identifier portion as a suffix portion, where the patient identifier portion is specific to the patient and the object identifier portion is specific to a medical record of the patient to contain the medical sensor data, the patient identifier portion being at least in part derived from the biometric data, the object identifier portion being at least in part derived from the medical sensor data, wherein the patient-specific HOI forms a single address defined by the prefix and suffix portions and that is resolvable to a unique network location via a domain name server;
   resolving the patient-specific HOI to an object location over a network at the unique network location based on the single address defined by the prefix and suffix portions; and
   writing the medical sensor data to the object location in real-time when the medical sensor data is acquired to auto-assemble the medical record of the patient.

* * * * *